US00PP19816P2

(12) United States Plant Patent
Noodelijk

(10) Patent No.: US PP19,816 P2
(45) Date of Patent: Mar. 10, 2009

(54) ***CHRYSANTHEMUM* PLANT NAMED 'GRANO RED'**

(50) Latin Name: *Chrysanthemum morifolium*
Varietal Denomination: Grano Red

(76) Inventor: Robert Noodelijk, Vrouwgeestweg 26, Woubrugge (NL), 2481 KN ( * ) Notice: Subject to any disclaimer, the term of this patent is extended or adjusted under 35 U.S.C. 154(b) by 0 days.

(21) Appl. No.: 12/001,651

(22) Filed: Dec. 12, 2007

(51) Int. Cl.
*A01H 5/00* (2006.01)

(52) U.S. Cl. ..... Plt./293

(58) Field of Classification Search ..... Plt./298, Plt./293

See application file for complete search history.

*Primary Examiner*—Kent L Bell
(74) *Attorney, Agent, or Firm*—Jondle & Associates, P.C.

(57) ABSTRACT

A *chrysanthemum* plant named 'Grano Red' characterized by its medium-sized blooms with greyed-red ray florets and prolific branching, a natural season flowering date of September 15, a blooming period of 6 weeks, a rounded plant habit, a spreading growth habit and a moderate growth rate, is disclosed.

1 Drawing Sheet

Genus: *Chrysanthemum morifolium.*
Variety denomination: 'Grano Red'.

BACKGROUND OF THE INVENTION

'Grano Red' is a product of a breeding and selection program for outdoor pot mums (garden mums) which had the objective of creating new *chrysanthemum* cultivars with a decorative type inflorescence, a natural season flowering date around September 15 and a blooming period of 6 weeks. The new plant of the present invention comprises a new and distinct cultivar of *chrysanthemum* plant.

'Grano Red' is a seedling resulting from the open pollination among groups of un-named and unpatented *chrysanthemum* cultivars maintained under the control of the inventor for breeding purposes. The new and distinct cultivar was discovered and selected as one flowering plant by Rob Noodelijk on a cultivated field in Woubrugge, The Netherlands in September 2005. The plant has been asexually reproduced by cuttings in greenhouses at Woubrugge, The Netherlands over a two year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Woubrugge, The Netherlands.

1. Large greyed-red inflorescences;
2. A rounded plant habit; and
3. A spreading growth habit and moderate growth rate.

DESCRIPTION OF THE PHOTOGRAPHS

The present invention of a new and distinct variety of *chrysanthemum* is shown in the accompanying photographs, the colors being as nearly true as possible with color photographs of this type.

DESCRIPTION OF THE INVENTION

Figure 1:
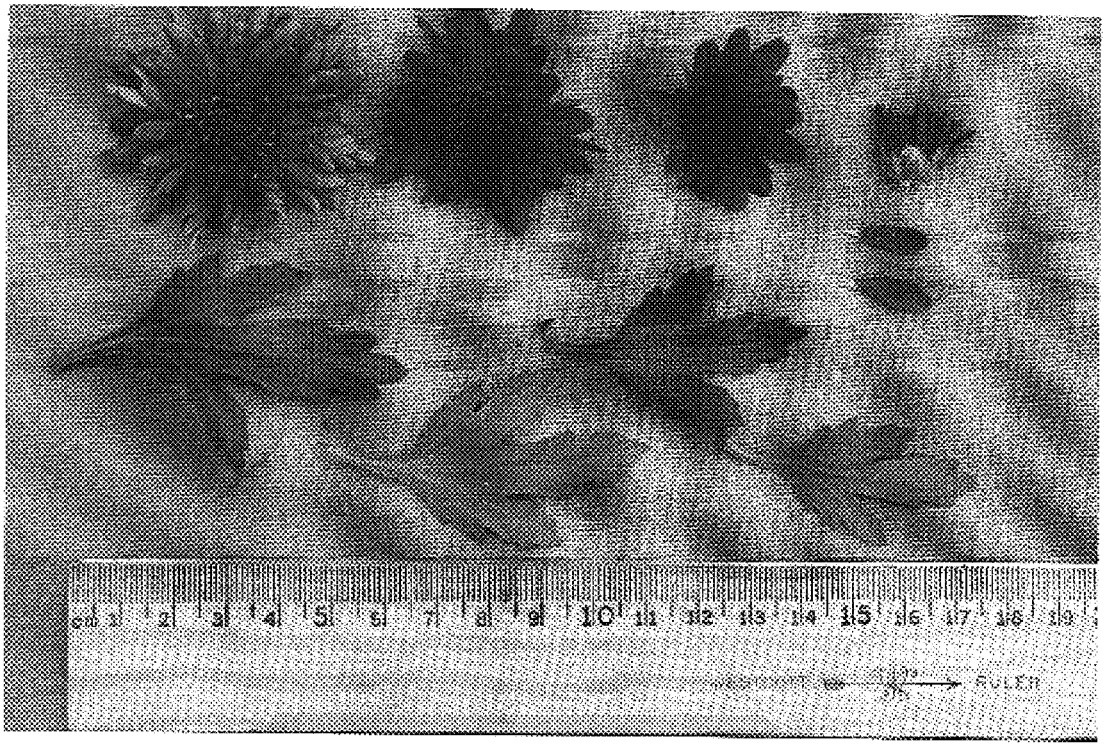
FIG. 1 shows a close-up of the individual inflorescences, florets, bud and leaves.
Figure 2:
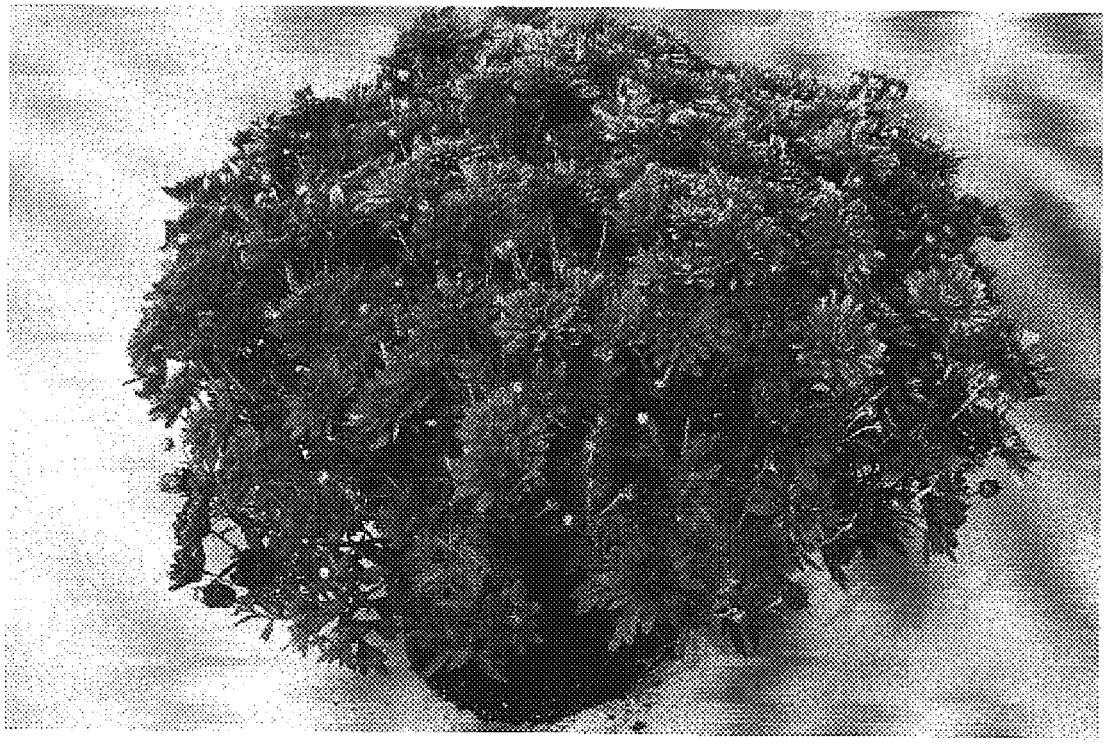
FIG. 2 shows a plant of the cultivar in full bloom.

This new variety of *chrysanthemum* is of the botanical classification *Chrysanthemum morifolium.* The observations and measurements were gathered from plants grown out door in Woubrugge, The Netherlands under natural day length and temperature and planted in week 22 in 2005 and 2006. The natural blooming date of this crop was September 15. The average height of the plants was 40 cm. No growth retardants were used. No tests were done on disease or insect resistance or susceptibility. No tests were done on cold or drought tolerance. This new variety produces medium-sized blooms with greyed-red ray florets and a red center blooming for a period of 6 weeks.

The following is a description of the plant and characteristics that distinguish 'Grano Red' as a new and distinct variety. The color designations are taken from the plant itself. Accordingly, any discrepancies between the color designations and the colors depicted in the photographs are due to photographic tolerances. The color chart used in this description is The Royal Horticultural Society color chart, edition 1995.

BOTANICAL DESCRIPTION OF 'GRANO RED'

Plant:
- *Shape.*—Rounded
- *Growth habit.*—Spreading.
- *Growth rate.*—Moderate.
- *Height.*—38 cm to 44 cm.
- *Width.*—44 cm to 48 cm.

Branches:
- *Stem.*—Color: RHS 137C (green). Strength: Strong. Brittleness: Branches are brittle. Anthocyanin coloration: Present; a slight layer of RHS 181A (greyed-red) mainly at the base of the stem.

*Length of lateral branch* (*from top to bottom*).—12 cm to 19 cm.
*Diameter of lateral branch.*—0.3 cm.
*Lateral branch color.*—RHS 137C (green).
*Lateral branch attachment.*—Petiolate.
*Branching (average number of lateral branches).*—Prolific with 10 breaks after pinching.

Leaves:
*Color.*—Upper surface: RHS 147A (yellow-green). Lower surface: RHS 137B (green).
*Size.*—General: Small to medium Length: 4.0 cm to 4.5 cm. Width: 1.0 cm to 1.3 cm.
*Quantity* (*number per lateral branch*).—7 to 8.
*Shape.*—Rhombic.
*Apex.*—Acute.
*Base.*—Acute.
*Margin.*—Serrate.
*Texture.*—Upper surface: Glabrous. Lower surface: Pubescent.
*Venation arrangement.*—Palmate.
*Shape of base of sinus between lateral lobes.*—Round.
*Margin of sinus between lateral lobes.*—Diverging.

Bud:
*Size.*—General: Medium. Cross-section: 1.5 cm. Height: 1.5 cm.
*Outside color.*—RHS 185A (greyed-purple).
*Involucral bracts.*—2 rows, length 0.6 cm, width 0.3 cm.
*Involucral bracts among disc-florets.*—Absent.
*Involucral bracts color.*—RHS 138A (green).

Bloom:
*Type.*—Double.
*size.*—General: medium. Fully expanded: 5.0 cm to 5.5 cm.
*Number of blooms per branch.*—Approximately 6 to 7 blooms per branch.
*Color of center of the inflorescence.*—Immature: RHS 185A (greyed-purple). Mature: RHS 185A (greyed-purple).
*Tonality from distance.*—A garden mum with red inflorescences.
*Discoloration to color.*—To RHS 172D (greyed-orange).
*Performance on the plant* (*blooming period*).—6 weeks.
*Fragrance.*—Typical *chrysanthemum*; slight.
*Peduncle.*—Length: 6 cm to 7 cm. Diameter: 0.2 cm. Color: RHS 137C (green).
*Natural season blooming date.*—September 15.

Ray florets:
*Texture.*—Both the upper and lower surfaces are smooth.
*Number.*—130 to 150.
*Cross-section.*—Flat to twisted.
*Longitudinal axis of majority.*—Straight.
*Color.*—Upper surface of the (outer) ray-florets: RHS 180A (greyed-red). Lower surface: RHS 180D (greyed-red).
*Length of corolla tube.*—0.2 cm to 0.3 cm.
*Apex.*—Round.
*Margin.*—Entire.
*Length.*—1.7 cm to 1.9 cm.
*Width.*—0.5 cm to 0.6 cm.
*Ratio length/width.*—High.

Disc florets: Absent.

Reproductive organs:
*Stamen* (*present in disc florets only*).—Absent.
*Pollen.*—Absent.
*Styles.*—Thin.
*Style color.*—RHS 144A (yellow-green).
*Style length.*—0.3 cm to 0.4 cm.
*Stigma color.*—RHS 144A (yellow-green).
*Stigma width.*—0.1 cm.
*Ovaries.*—Enclosed in calyx.

Fruit/Seed set: Seeds are produced in small quantities; ovate, RHS 199A (grey-brown) and 0.15 cm in length.

COMPARISON WITH COMMERCIAL CULTIVARS

'Grano Red' differs from the commercial cultivar 'Yotabitha' (U.S. Plant Pat. No. 16,110) in that 'Grano Red' flowers earlier (September 15) than 'Yotabitha' (September 24). Additionally, 'Grano Red' has large (up to 5.5 cm) greyed-red inflorescences, while 'Yotabitha' has smaller (up to 4 cm) red-purple inflorescences.

I claim:

1. A new and distinct variety of *chrysanthemum* plant as described and illustrated.

* * * * *